United States Patent [19]

Davis, Jr. et al.

[11] Patent Number: 4,490,676
[45] Date of Patent: Dec. 25, 1984

[54] MICROWAVE MEANS FOR MONITORING FLUID IN A CORE OF MATERIAL

[75] Inventors: Lorne A. Davis, Jr.; Dale F. Brost; Helen K. Haskin, all of Houston, Tex.

[73] Assignee: Texaco Inc., White Plains, N.Y.

[21] Appl. No.: 336,142

[22] Filed: Dec. 31, 1981

[51] Int. Cl.³ .................. G01V 3/17; G01R 27/00; G01N 27/00
[52] U.S. Cl. .................. 324/376; 324/58.5 A
[58] Field of Search .......... 324/58 R, 58 A, 58.5 R, 324/58.5 A, 334, 338, 376; 73/153

[56] References Cited

U.S. PATENT DOCUMENTS

| | | | |
|---|---|---|---|
| 2,165,214 | 7/1939 | Blau et al. | 324/58.5 A X |
| 2,963,641 | 12/1960 | Nanz | 324/376 |
| 3,360,721 | 12/1967 | Pullman | 324/58.5 A |
| 3,501,692 | 3/1970 | Kluck | 324/58.5 A |
| 3,818,333 | 6/1974 | Walker | 324/58.5 A |
| 4,131,845 | 12/1978 | Pakulis | 324/58.5 A |

Primary Examiner—Gerard R. Strecker
Attorney, Agent, or Firm—Jack H. Park; Ronald G. Gillespie

[57] ABSTRACT

A microwave core monitor includes a sample cell which contains a test core of an earth formation. A microwave transmitter irradiates the test core with a beam of electromagnetic energy at a microwave frequency. A microwave receiver provides an indication representative of a characteristic of a liquid, or the absence of a liquid, in the test core in accordance with electromagnetic energy that has passed through the core. The sample cell further includes microwave absorber rods which prevent portions of the beam of electromagnetic energy not passing through the test core from reaching the receiver.

20 Claims, 10 Drawing Figures

MICROWAVE MEANS FOR MONITORING FLUID IN A CORE OF MATERIAL

BACKGROUND OF THE INVENTION

1. Field of the Invention

The present invention relates to earth formation analysis in general and, more particularly, to microwave spectrometry of an earth formation core and to surfactant testing.

2. Prior Art

Heretofore a method of analyzing in situ oil-brine saturation of samples of an earth formation in a laboratory were of the type described by R. W. Parsons, MICROWAVE ATTENUATION—A NEW TOOL FOR MONITORING SATURATIONS IN LABORATORY FLOODING EXPERIMENTS, Society of Petroleum Engineering Journal (August 1975, Volume 15, 302–309). However, these instruments are based upon a microwave frequency of about 21 GHz. Several difficulties arise from the high power level required at this frequency to penetrate the water-saturated rock slabs used in the experiments. Power levels are on the order of several hundred millawatts, far above established safe exposure limits. Because of this, adequate precaution must be taken to insure a safe working environment. The use of high power levels cause several instrumental complications.

To generate several hundred milliwatts of microwave power at 21 GHz, klystron sources are used which require specialized power supplies for stable operation and also requires considerable maintenance. Further since a wide range of power is transmitted through a core during a flooding experiment, precision attenuators are required to maintain the power level within the range limits of the detector. Isolators must be used to shield the klystron from reflective radiation. Tuners are employed to precisely match impedances from maximum power transfer efficiency. Microwave power is directed to and from the porous medium by lens-corrected directional horns. Transmitted power is detected by a thermocouple or crystal based power meter, converted to a voltage and passed to a logarithmic amplifier. The output is proportional to the water saturation of the core.

In addition to the undesirable expense and complexity of the aforementioned designs, practical application has been restricted to epoxy-coated flat slabs of Berea sandstone having typical dimensions of 2.54 cm thick, 10.2 cm wide and up to 122 cm long.

The present invention by utilizing a small cross-sectional area test core is capable of operating throughout the microwave frequency range at lower power level than Parsons and does not require the safety equipment nor the complex instrumentation required in the aforementioned Parsons apparatus. The present invention eliminates isolators and does not have to be tuned.

SUMMARY OF THE INVENTION

An earth formation microwave core monitor includes a sample cell which contains a test core of an earth formation. A microwave transmitter irradiates the test core with a beam of electromagnetic energy. A microwave receiver provides an indication representative of a charateristic of a liquid, or the absence of a liquid, in the test core in accordance with electromagnetic energy that has passed throught the sample cell. The sample cell further includes microwave absorbers which prevent portions of the microwave beam not passing through the test core from reaching the receiver means.

One object of the present invention is to provide a microwave core monitor for determining a characteristic of a test core of an earth formation.

Another object of the present invention is to provide a microwave core monitor suitable for use in a laboratory or in the field.

A further object of the present invention is to provide a rapid and simple method of surfactant testing to aid in surfactant selection prior to chemical flooding of a petroleum reservoir in enhanced oil recovery.

Another object of the present invention is to provide a low power level microwave core monitor for utilization with substantially small size cores of an earth formation.

The foregoing and other objects and advantages of the invention will appear more fully hereinafter from a consideration of the detail description which follows, taken together with the accompanying drawing wherein two embodiments of the present invention are illustrated by way of example. It is to be expressly understood, however, that the drawings are for illustration purposes only and are not to be construed as defining the limits of the invention.

DESCRIPTION OF THE INVENTION

Figure 1:
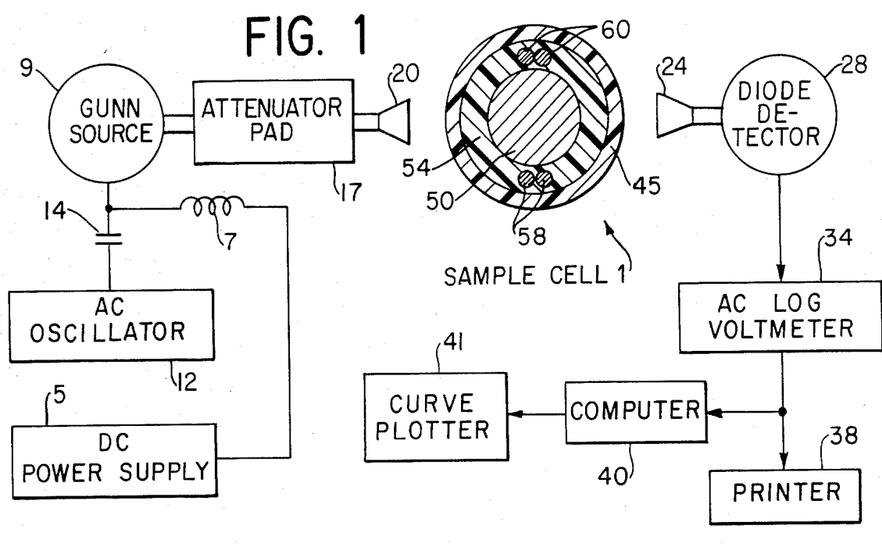
FIG. 1 is a simplified block diagram of a microwave core monitor constructed in accordance with the present invention.

Referring now to FIG. 1, a sample cell 1 constructed as hereinafter disclosed, is subject to microwave energy. Microwave energy is herein defined as being electromagnetic energy provided at a microwave frequency. In providing microwave energy, a direct current current supply 5 provides DC power through a coil 7 to a Gunn microwave source 9 of the type that is manufactured by Racon, Inc. as their part number 10014-102-02. An oscillator 12 provides an AC voltage as a predetermined frequency through a capacitor 14 to Gunn source 9. A preferred frequency of the AC voltage is 1 KHz. Gunn source 9 provides the microwave energy, at a preferred frequency of 10.525 GHz, whose amplitude oscillates at the 1 KHz frequency. Source 9 provides the microwave energy to an attenuator pad 17 which provides the microwave energy in turn to a horn antenna 20. It should be noted that a horn antenna is used because the Gunn source 9 is being operated in an X-band mode. It may be desired to operate Gunn source 9 at a preferred frequency of 24.125 GHz, which is in the K-band mode and makes monitoring more independent of temperature and salinity in regards to the sample in sample cell 1. The determination of whether to use X-band or K-band is also in part determined by the core size selected. A preferred power output for the X-band is 10 mw while for the K-band is anything greater than 50 mw to safe operating levels. Horn antenna 20 is replaced by a dielectric rod antenna and Gunn source 9 is of a type similar to that manufactured by Plessey Optoelectronics and Microwave Ltd., as their part GDO131 when operating in a K-band mode. Further, oscillator 12 may be omitted in K-band operations.

The microwave energy passing through sample cell 1 is received by another horn antenna 24 in X-band mode, or a dielectric rod antenna in the K-band mode, and provided to a diode detector 28. Diode detector 28 provides an electrical signal, corresponding to the detected microwave energy, to an AC log voltmeter 34. Voltmeter 34 provides a visual readout and also an output to a printer 38 and to a computer 40 which prints out the detected microwave energy. Computer 40 controls a curve plotter 41 in accordance with the output from voltmeter 34.

Figure 2:
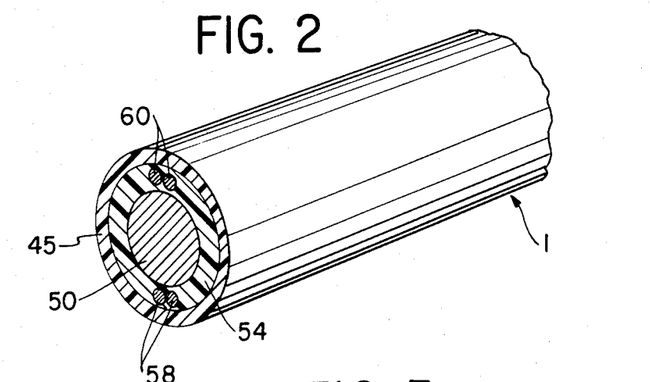
FIG. 2 is a graphical representation of the sample cell shown in FIG. 1.

Referring now to FIGS. 1 and 2, sample cell 1 includes a cylindrical test core 50 of an earth formation, having a preferred diameter in the range of from a ½ inch to ¾ inch and a preferred length in the range from 2¾ inches to 3 inches, is maintained in a hard plastic tubular shell 45 by epoxy 54. Another way to define the length is to say that the length is substantially equal to the distance along the longitudinal axis of test core 50 that is intercepted by the microwave beam. Shell 45 may be made of a machineable hard plastic such as chlorinatedpolyvinylchloride or polyvinylidinediflouride. Embedded in epoxy 54 are absorber rods 58 and 60. In one particular application there are four such microwave absorber rods 58 and 60. One pair of absorber rods 58 are located along side of test core 50 while another pair of absorber rods 60 are located diametrically opposite along side of test core 50. It should be noted that test core 50 is oriented with relation to antenna 20 and 24 in a manner so that a straight line from antenna 20 to antenna 24 will be perpendicular to an axis passing through both pairs of absorber rods 58 and 60. Absorber rods 58 and 60 prevents the microwave energy from circumventing the core 50 and being detected by diode detector 28 so as not to cause erroneous readings and so that the microwave energy detected by detector 28 is the microwave energy that has passed through test core 50. Microwave absorber rods 58 and 60 are made of ferrite loaded epoxy. Preferred attenuation coefficient for such material is 46 dB/cm at 10 GHz.

The apparatus as hereinbefore described may be used to screen surfactants prior to core flood testing and has the following advantage: (1) the actual formation material is used to test the surfactants, (2) the screening is rapid and (3) highly economical.

Figure 3:
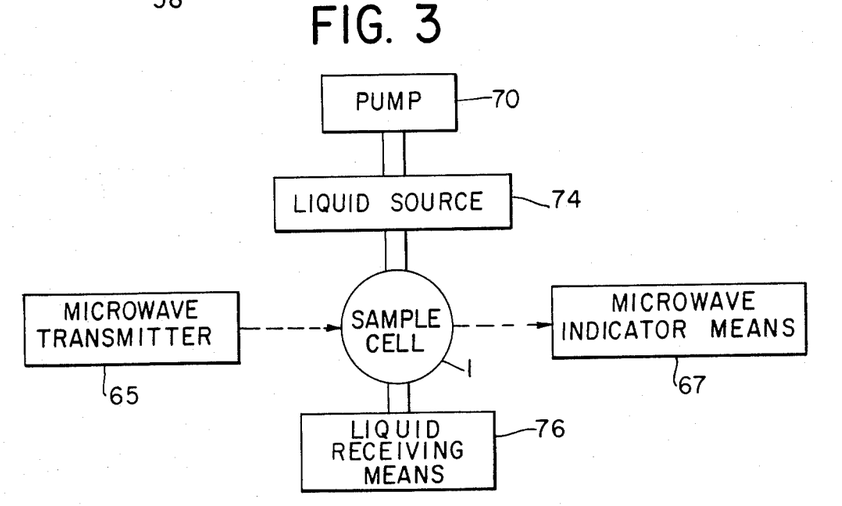
FIG. 3 is a simplified block diagram of a surfactant monitor, constructed in accordance with another embodiment of the present invention.

In this regard, and with reference to FIG. 3, microwave transmitter 65 includes DC power supply 5, coil 7, Gunn source 9, AC oscillator 12, capacitor 14, attenuator pad 17 and antenna 20, all of which function as previously described. A microwave indicator means 67 includes antenna 24, diode detector 28, AC log voltmeter 34 and printer 38; all of which function as previously described. A pump 70 pumps distilled water to a liquid source 74. Liquid source 74 includes a conventional type free floating piston (not shown) in a container (not shown) having a liquid. The pumped in distilled water causes the piston to expell the liquid from liquid source 74. Further liquid source 74 is capable of readily having one liquid replaced by another liquid for reasons hereinafter explained.

The expelled liquid from liquid source 74 enters sample cell 1, which is adapted as hereinafter explained for the surfactant tester of FIG. 3, until sample cell 1 is completely filled. Excess liquid will pass through sample cell 1 into liquid receiving means 76 which may be test tubes or any other suitable container.

Figures 4, 5, 6:
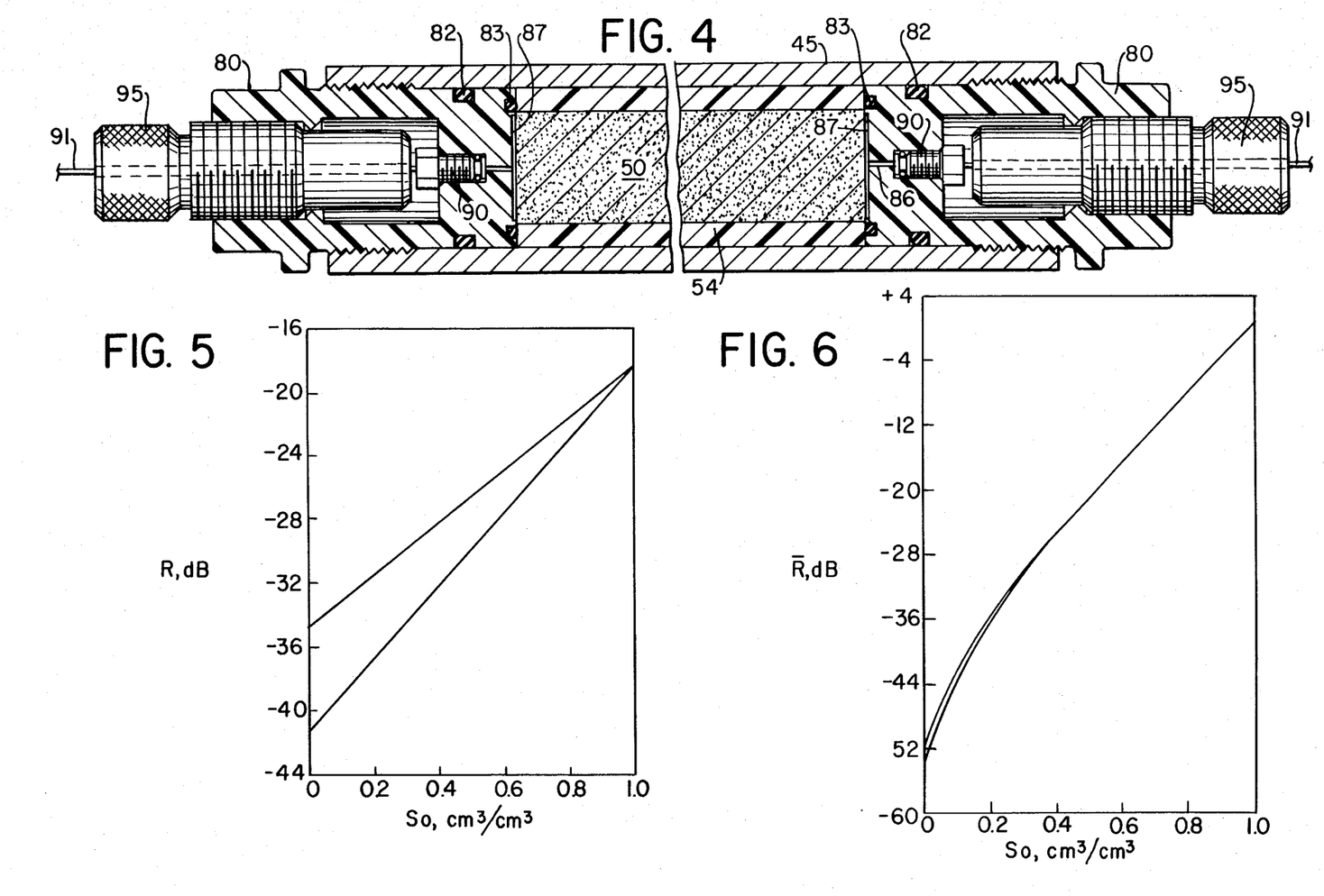
FIG. 4 is a detailed drawing of the sample cell shown in FIG. 1.
FIGS. 5 and 6 are graphs of typical calibration curves for the operation of the present invention in X-band and K-band microwave modes, respectively.

Referring now to FIG. 4, shell 45 is machined to have female threads at both ends and test core 50 is centered in shell 45 and held in place by epoxy 54 containing absorber rods 58 as hereinbefore described. End plugs 80 are screwed into shell 45 at each end with O-rings 82 and 83 in place. O-rings 82 provides sealing between shell 45 and end plugs 80 so that no liquid can escape from sample cell 1 while O-rings 83 provides sealing between epoxy 54 and end plugs 80 so that the liquid flows through test core 50.

Each end plug 80 has a channel 86 from an internal face 87 to a bottom tap where a convential type chromatograph fitting 90 is seated having tubing 91 connected to it. Tubing 91 passes through a support bolt 95 which is made of machineable plastic and adapted to be threaded into end plug 80. Support bolt 95 holds chromatograph fitting 90 in place inside end plug 58 and supports tubing 91 as it passes through support bolt 95. The entire end plug-support bolt assembly has a very low dead volume as compared to a conventional manner of providing end plugs for sample cell 1. Dead volume is any volume in the test arrangement that is not the pore volume of test core 50. Large dead volume can render pore volume determination and usage erroneous.

SURFACTANT SCREENING

Production of crude oil from a reservoir in an earth formation generally will experience several phases. In an initial phase the natural reservoir pressures, the porosity of the reservoir's earth formation and the fluidity of the crude oil permits production without assistance other than pumping. However, there comes a time when there is still considerable crude oil in the reservoir, but the pressure is such that assistance is necessary. The assistance is provided with a water flood in a secondary recovery operation using a drive liquid, such as salt water, to drive the crude oil to a producing well.

Even after secondary recovery operations, there still remains considerable in-place crude oil. At this time most reservoirs are subjected to enhanced oil recovery operation using a chemical flood. A chemical flood utilizes a surfactant which is driven through the reservoir by a liquid, usually salt water, with a polymer slug between the drive liquid and the surfactant. The surfactant decreases the interfacial tension between the crude oil and the in-place brine in the reservoir's earth formation so that the crude oil so released is driven to the producing well. Again not all of the in-place crude oil is so affected so that even after a chemical flood there is residual crude oil in the reservoir.

There are many different types of surfactants that will react with the crude oil, the salt water and the reservoir's earth formation in different ways. Many tests are conducted to select the best surfactant for a particular reservoir. However, the tests are lengthy. The present invention, as hereinafter described, provides an initial screening process so that only those surfactants showing promise for use in the reservoir need be subjected to the longer time consuming tests.

With reference to FIG. 3, sample cell 1 is already in existence or, preferable made in which test core 50 is obtained from the reservoir's earth formation where a selected surfactant is intended to be used. Initially, microwave transmitter 65 irradiates sample cell 1 while sample cell 1 has no liquid in it so that a first reading is obtained from microwave indicating means 67 of test core 50 of sample cell a as if it were filled only with oil. Initially, the liquid in liquid source 74 is salt water, preferably of substantially the same salinity and hardness as the water used to flood the reservoir where a selected surfactant will be used, the salt water is pumped into sample cell 1 at an arbitrarily selected velocity of 20 feet per day. Microwave transmitter 65 is still irradiating sample cell 1 with microwave energy. When salt water appears entering liquid receiving means 76, a second reading provided by microwave indicating means 67 is representative of the salt water in sample cell 1.

The liquid in liquid source 74 is changed from salt water to crude oil from the reservoir and pump 70 is operated until only crude oil enters liquid receiving means 76. A third reading provided by microwave indicating means 67 at this time is representative of residual salt water to oil injection. A conventional material balance is carried out at this time to provide an oil saturation measurement.

The crude oil in liquid source 74 is replaced with salt water and the operation is repeated, i.e., until only salt water enters liquid receiving means 76, a fourth reading at this time corresponds to residual oil to water flood. Again, a material balance yields a measurement of the new oil saturation.

The four readings along with the material balance measurements constitute calibration data. Computer 40 controls curve plotter 41 to generate a curve in accordance with the calibration data. FIGS. 5 and 6 show typical calibration curves for X-band and K-band operation respectively.

The next step of surfactant screening is to pump a surfactant into sample cell 1 from liquid source 74 at the test core 50 so as to standardize the screening of the surfactants. No reading is necessary at this time. A post-surfactant flush is then initiated using salt water having substantially the same salinity as the expected surfactant drive water in the field. A reading is taken when no further oil enters liquid receiving means 76 which is then utilized with the generated calibration graph to determine the residual oil saturation after chemical flood.

By using the foregoing method, several different sample cells 1 may be constructed from the reservoir earthen material since test core 50 is small in size. This facilitates screening of different surfactants.

In another embodiment, only one particular sample cell 1 is used to test the different surfactants. In this method the calibration readings, and hence computer 40 and curve plotter 41, may be eliminated and the readings of residual oil saturation after chemical flood may be used directly in the selection of a surfactant. This method requires the following summarized steps for each surfactant test.

1. Saturate test core 50 with salt water.
2. Flood test core 50 with crude oil to residual water.
3. Flood test core 50 with salt water to residual oil to water flood.
4. Flood test core 50 with surfactant.
5. Flush surfactant from test core 50 with salt water.
6. Obtain a reading from microwave indicating means 67 which is representative of the residual oil saturation after chemical flood.
7. Wash test core 50 of sample cell 1.

The washing step is accomplished by washing with fresh water at maximum rate that pressure will allow. After clean water leaves sample cell 1, 2-propanol is flushed through sample cell 1 to remove any absorbed surfactant. A preferred mixture of 80% toluene and 20% methanol by volume is flushed through test core 50 of sample cell 1 to wash out residual crude oil followed by another wash of 2-propanol. Finally test core 50 in sample cell 1 is washed with fresh water and sample cell 1 is then ready to be used for surfactant screening again.

CORE FLOOD TESTING

Since it is desirable that a portion of the reservoir formation be subjected to a flooding test, the Parsons instrumentation could not be used since it requires a slab of the formation. Such a slab either cannot be obtained from a reservoir's formation or it is not readily obtainable. The conventional alternative to Parsons is to use a field core from the reservoir formation and test it using a material balance technique. However, because of the small quantities of liquid used in the conventional core flood testing the associated error in determining the tertiary oil recovery efficiency may be well in the neighborhood of 16%.

The present invention provides the same information as the conventional core flood test such as the initial oil saturation before water flood averaged over the core length, the residual oil saturation after the water flood averaged over the core length, the residual oil saturation of the chemical flood averaged over the core length, and water flood and chemical flood recovery efficiency, which is the ratio of the amount of oil removed to the amount of oil in place with greater accuracy in the neighborhood of 1%. The present invention further provides an indication of oil saturation distribution along the length of the test core.

Further, the conventional core flood method utilizes a core one to six feet long which covers the stratum but is not representative of the formation at a particular level within the stratum so that there is an average determination. The present invention, since it uses small cores as hereinafter explained, can reduce the level within the stratum to a matter of inches as opposed to the several feet used in the conventional method. Further, several cores can be made utilizing the present invention as opposed to a conventional type of core resulting in greater economy.

Figures 7, 8:
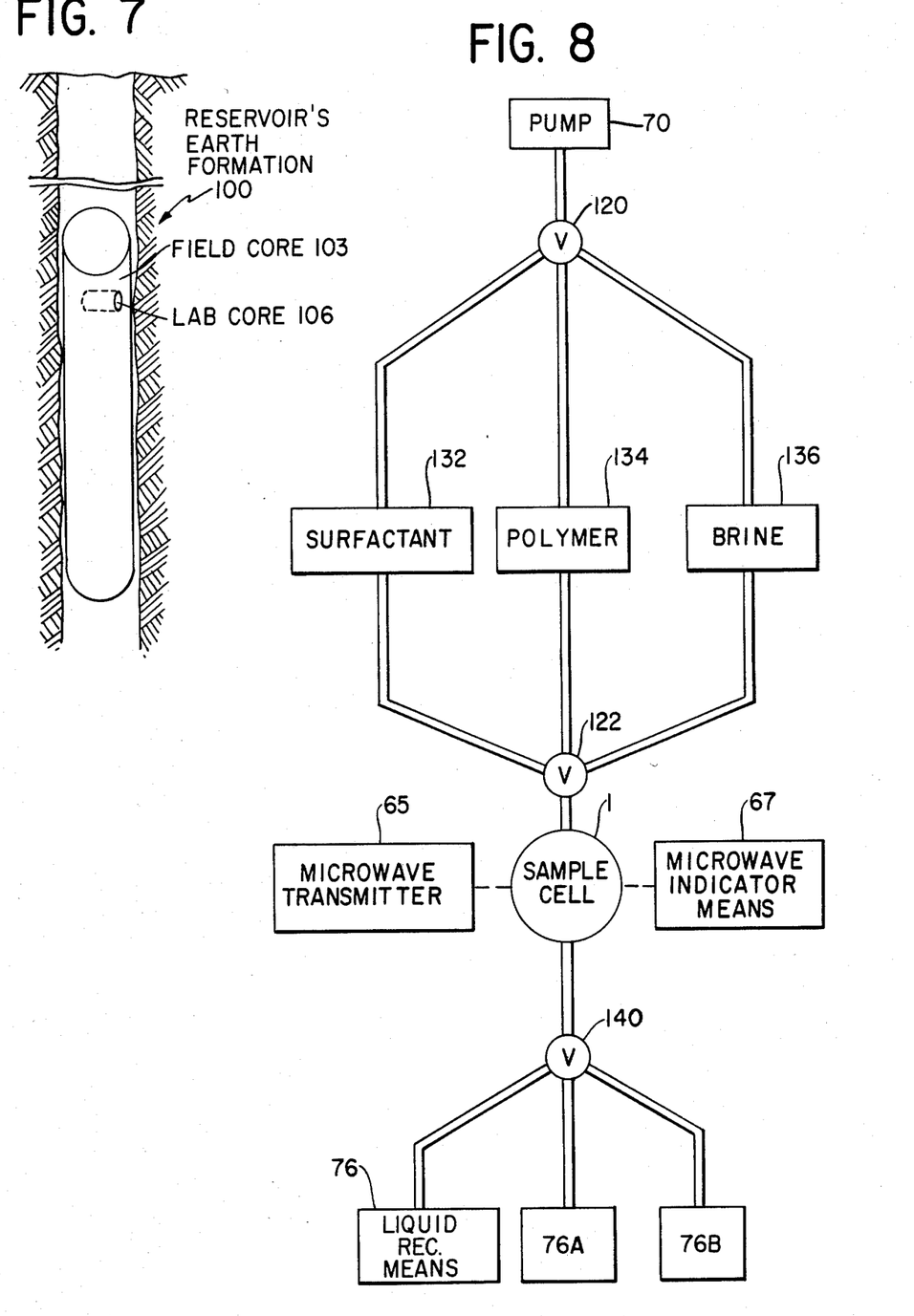
FIG. 7 illustrative shows the relationship of a field core, a lab core and a reservoir's earth formation.
FIG. 8 is a simplified block diagram of a core flood tester constructed in accordance with the present invention.
Figure 9A:
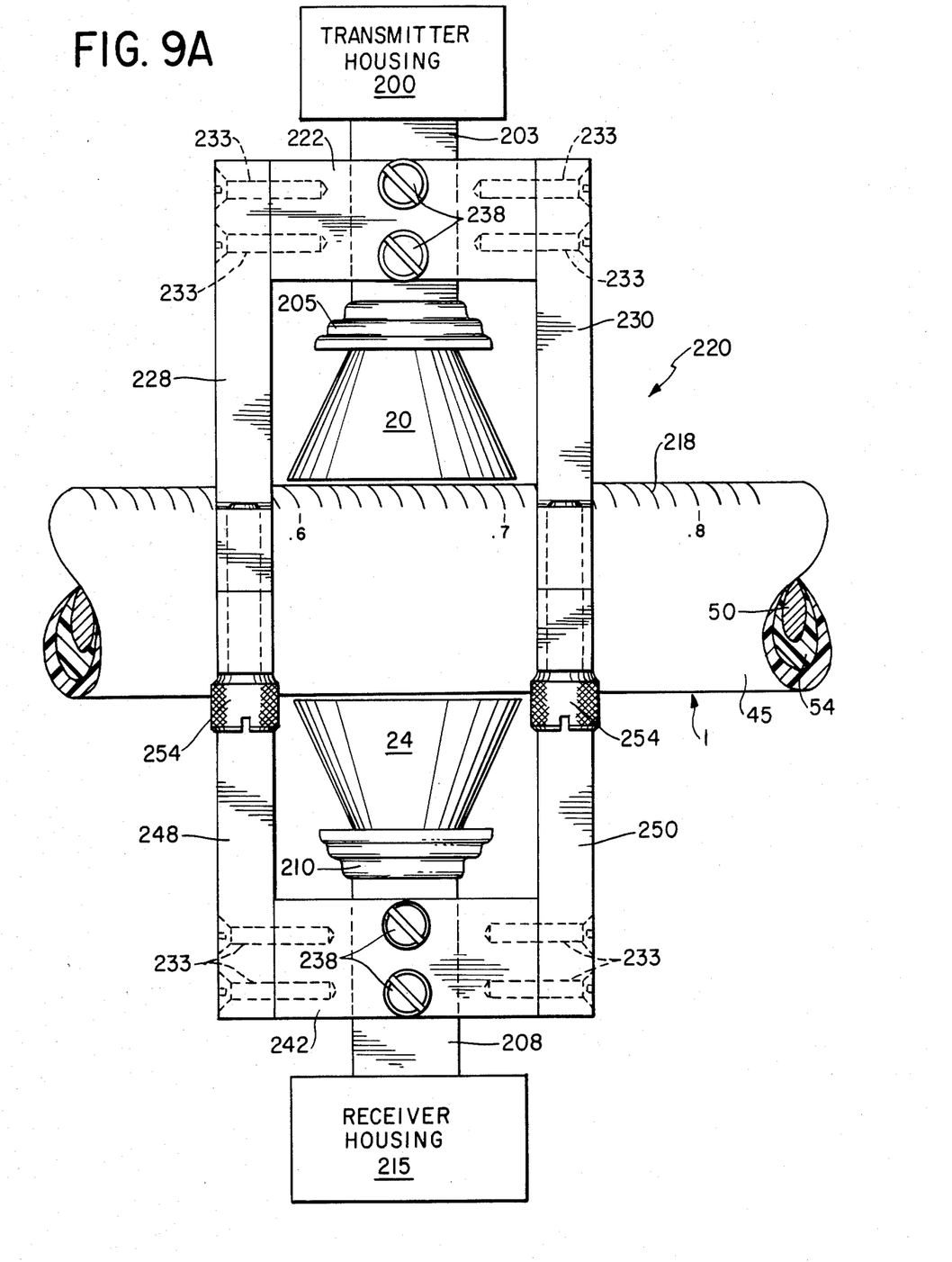
FIGS. 9A and 9B are assembly type drawings of a fixture used in the core flood tester.
Figure 9B:
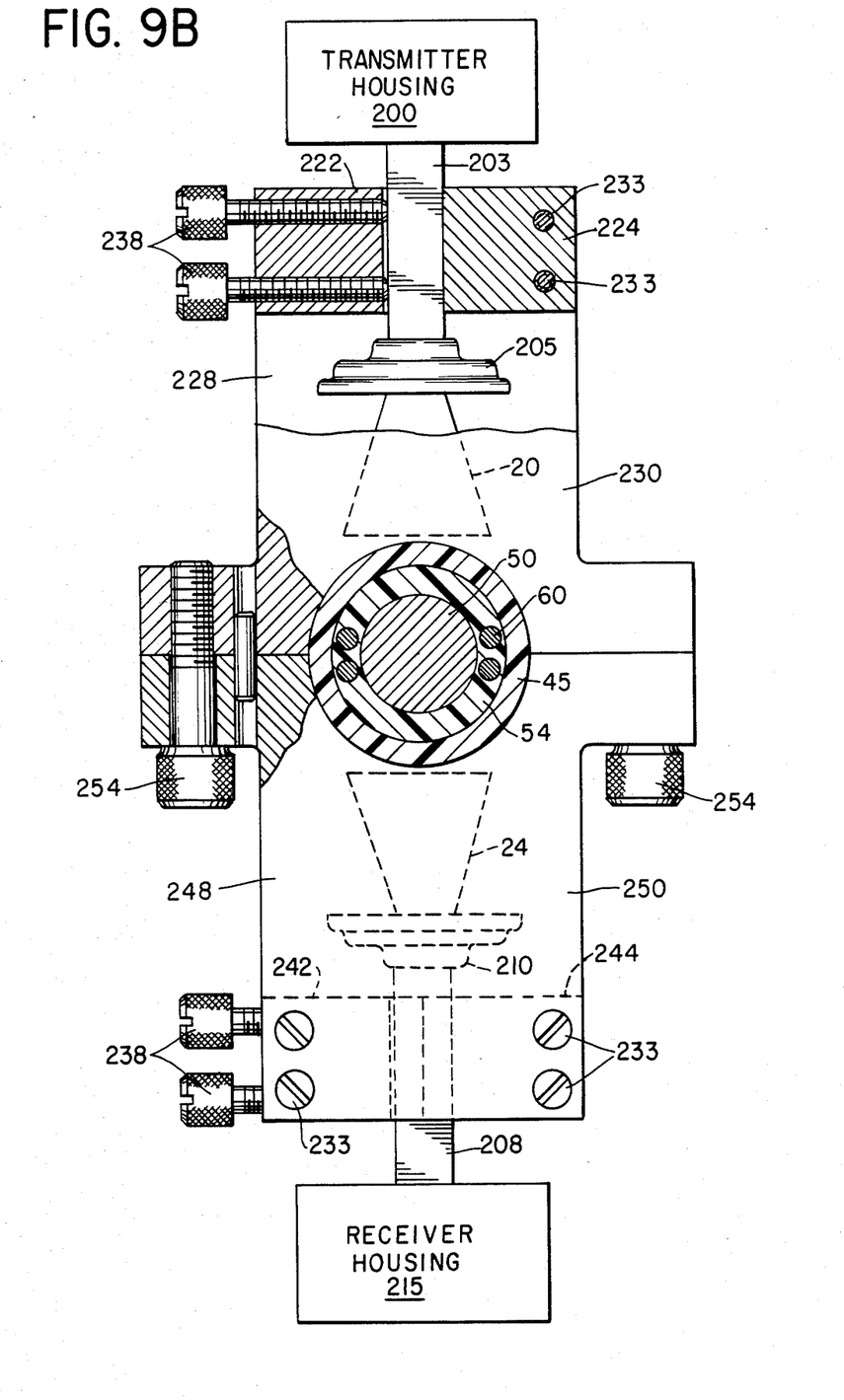

Referring to the FIG. 7, a reservoir's earth formation 100 has a field core 103 removed from it by conventional coring methods. FIG. 7 also shows the relationship of field core 103 to the reservoir's earth formation 100. Field core 103 is then cored in a laboratory or any suitable location to extract lab core 106. As noted previously in describing test core 50, which essentially is made up of lab cores 106 for cylindrical test core 50, has a preferred diameter in the range of from a one-half inch to three-quarter inch. If test core 50 has rectangular cross section, lab core 106 will also have rectangular cross section having one side a preferred size of three- The prior description contemplates operation at microwave frequencies in the X-band. As noted previously, gunn source 9 may be operated in the K-band during which all of the comments previously mentioned for K-band operation are equally applicable.

With reference to FIG. 8 valve means 120 and 122 are operated in conjunction with pump 70 to provide a small slug size of surfactant from surfactant source 132 to sample cell 1. A preferred size of the slug is approximately ⅓ of the pore volume of long core 114 in sample cell 1. Valves 120 and 122 are then operated to provide the surfactant slug with polymer interface slug from polymer source 134 to sample cell 1 and through it. Again valve means 120 and 122 are then operated to drive the polymer and surfactant slugs with brine from brine source 136. All of the driving is done at a standard frontal velocity which by way of example maybe is roughly the flooding velocity of the reservoir. In this case, the selected velocity is 4 feet per day. That velocity may be restated as being 0.033 inch/minute. Since the liquids are moving at a slow frontal advance speed through test core 114, a fixture 198 is utilized to periodically scan sample cell 1 and readings are taken at predetermined intervals of sample cell 1.

Another application of the present invention is to use a slug size of 1/10 the pore volume of test core 114 in a core flood test and then determine the recovery efficiency at every tenth of the length of test core 114. A graph of the recovery efficiency versus slug size may be then developed. For example at 1/10 of the length of test core 114, the equivalent slug size is 1 pore volume and at 7/10 of the length, the equivalent slug size is 1/7 of the pore volume. The plotting of the slug size characteristics of different surfactants and/or polymer mobility control agent may then be used in selecting a suitable surfactant and/or polymer system.

The device of the present invention is a small core microwave monitor which may be used in the field or in the laboratory and which also may be used for surfactant screening or core flood testing.

An alternative method of calibration of multiple test core 50 prior to surfactant screening for K-band operation is
1. Saturate test core 50 with fresh water.
2. Flood with a predetermined mixture of 2-propanol and fresh water.
3. Obtain a reading from microwave indicating means 67 which is representative of oil saturation.

Steps 2 and 3 are repeated for different mixtures of 2-propanol and fresh water. As can be seen from the foregoing there are no material balance measurements required for calibration. At this point, the multiple core testing may be carried on as hereinbefore described.

The present invention may even be used at simulated field conditions of temperature to screen surfactants. The present invention as hereinbefore described can stand up to 300 psi of pressure. The present invention may also be used in an oven and the temperature raised to simulate reservoir temperature for the screening of surfactants. However, it should be noted that if the test temperature is close to or greater than the temperature ratings of the components of the microwave system, then an oven may be constructed in which only sample cell 1 is located in the oven and the microwave energy is directed through the walls of the oven and through sample cell 1.

What is claimed is:
1. An earth formation core monitor comprising:
a sample cell which includes a core of an earth formation containing a liquid,
transmitter means for irradiating said core with a beam of microwave energy, and
receiver means spatially related to said sample cell for receiving a beam of microwave energy after it has passed through said sample cell and for providing an indication representative of a characteristic of the liquid of said core in accordance with received microwave energy, and
said sample cell also includes means spatially related to said core for preventing any portion of said irradiating beam of microwave energy not passing through said core from being received by said receiver means.

2. A monitor as described in claim 1 in which said sample cell further includes
a shell in which the core is situated, and
epoxy material maintains the core within the housing; and
in which the preventing means are absorber rods located in the epoxy material in such a manner that the microwave absorber rods are at diametrically opposite sides of said sample cell and said sample cell is arranged so that the longitudinal axis of the irradiating beam of microwave energy is passed between the absorber rods.

3. A monitor as described in claim 2 in which the transmitter means includes microwave source means for providing microwave energy,
an antenna connected to the source means provides the microwave energy from the source means as the beam of microwave energy, and
attenuating means connected between the source means and the antenna for controlling the microwave energy provided to the antenna means so as to control the strength of the irradiating beam of microwave energy.

4. A monitor as described in claim 3 in which the receiver means includes detector means for detecting the beam of microwave energy that has passed through said core and for providing an electrical signal in accordance with the detected microwave energy.
AC logarithmic voltmeter connected to the detector means and providing a visual display represented of the detected microwave beam in accordance with the electrical signal and providing a corresponding electrical output, and,
printing means connected to said voltmeter for making a printed record of the reading of the voltmeter in accordance with the electrical output.

5. A monitor as described in claim 4 in which the core does not contain a liquid and further comprising liquid fill means connected to said sample cell for filling said core with a liquid.

6. A monitor as described in claim 5 in which said liquid fill means include
a liquid source means connected to the sample cell for containing a liquid,
pump means connected to said liquid source means for causing said liquid source means to provide a liquid contained therein to said sample cell, and
liquid receiving means connected to said sample cell for receiving liquid from said sample cell so that when the pump means causes the liquid source means to provide the liquid to said sample cell, the receiving of the liquid by the liquid receiving means is indicative that the core in said sample cell is full with the liquid.

7. A monitor as described in claim 6 in which the microwave source means includes
first voltage means for providing a direct current voltage,
means for providing an alternating current voltage, and,
a Gunn oscillator connected to both voltage means and to the attenuating means and rendered operational by both voltages to provide microwave energy to the attenuating means.

8. A monitor as described in claim 7 in which the detector means includes an antenna receiving the portion of the beam of microwave energy that has passed through said core and providing a corresponding output, and,
a diode detector connected to the antenna provides the electrical signal in accordance with the received microwave energy.

9. A monitor as described in claim 8 in which the microwave transmitter means is operated so that the microwave energy is within the X-band of microwave frequencies, and the antennas in the transmitter means and in the receiver means are horn antennas.

10. A monitor as described in claim 8 in which transmitter means provides the microwave energy within the K-band of microwave frequencies and the antennas in the transmitter means and the receiver means are dielectric rod antennas.

11. A monitor as described in claim 8 in which the core is cylindrical in shape.

12. A monitor as described in claim 11 in which the diameter of the core is within a preferred range of ½ of an inch to ¾ of an inch, and,
the length of the core is within a preferred range of 2¾ inches to 3 inches.

13. A monitor as described in claim 8 in which the core has a rectangular cross-section and a predetermined length.

14. A monitor as described in claim 13 in the rectangular cross-section of the core having one preferred side dimension of ¾ of an inch,
another perferred side dimension of ⅝ of an inch, and
a length within a preferred range of 2¾ inches to 3 inches.

15. A monitor as described in claim 4 in which the core does not contain a liquid; and,
further comprising a plurality of liquid sources connected to the sample cell, each liquid source containing a different type of liquid, and,
pump means connected to said liquid sources for causing said liquid sources to provide the liquids to said sample cell in a predetermined sequence at a predetermined flow rate.

16. A monitor as described in claim 15 in which the length of the sample cell lies within the preferred range of two to six feet, and
further comprising means for moving portions of the transmitter means and of the receiver means along the length of the sample cell in a manner so that the beam of microwave energy may be passed through said core in said sample cell at predetermined intervals of such.

17. A monitor as described in claim 16 further comprising computer means connected to the detector means for providing information representative of the characteristics of the liquid flowing through the sample cell in accordance with the signal from the detector means.

18. A monitor as described in claim 17 in which the fixture means includes a first housing adapted to the sample cell contains the portion of the transmitter means,
a second housing adapted to said sample cell contains the portion of the receiver means, and,
means for clamping the two housings together in a manner so that the receiver means and the transmitter means are aligned and so that both housings are readily moveable along the length of said sample cell so that the characteristics of the liquids flowing through the sample cell may be determined at the various intervals of the sample cell.

19. An earth formation core monitor comprising:
a sample cell which includes a core of an earth formation containing at least one liquid,
transmitter means for irradiating said core with a beam of microwave energy,
receiver means spatially related to said sample cell for receiving a beam of microwave energy after it has passed through said sample cell and for providing an indication representative of a characteristic of the liquid of said core in accordance with receive microwave energy, and
means spatially arranged with said core for preventing any portion of said irradiating beam of microwave energy not passing through said core from being received by said receiver means.

20. A monitor as described in claim 1 in which said sample cell further includes
a shell in which the core is situated, and
epoxy material maintains the core within the housing; and
in which the preventing means are absorber rods located in the epoxy material.

* * * * *

UNITED STATES PATENT AND TRADEMARK OFFICE
CERTIFICATE OF CORRECTION

PATENT NO. : 4,490,676
DATED : December 25, 1984
INVENTOR(S) : L. A. DAVIS: D. F. BROST: H. K. HASKIN It is certified that error appears in the above—identified patent and that said Letters Patent is hereby corrected as shown below:

Column 10, line 44 "energy." should read --energy,--

Column 10, line 49 "and," should read --and--

Signed and Sealed this

Seventh Day of May 1985

[SEAL]

Attest:

DONALD J. QUIGG

Attesting Officer     Acting Commissioner of Patents and Trademarks